(12) United States Patent
Andersohn

(10) Patent No.: US 8,512,302 B2
(45) Date of Patent: Aug. 20, 2013

(54) DEVICE FOR COLLECTION OF ASPIRATED FLUIDS

(75) Inventor: Lutz Andersohn, Glencoe, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 972 days.

(21) Appl. No.: 12/332,853

(22) Filed: Dec. 11, 2008

(65) Prior Publication Data

US 2010/0152648 A1    Jun. 17, 2010

(51) Int. Cl.
*A61M 1/00* (2006.01)

(52) U.S. Cl.
USPC ........... 604/319; 604/187; 604/192; 604/268; 604/289; 604/290; 604/296; 604/300; 604/304; 604/305; 604/311; 604/312; 604/313; 604/315; 604/316; 604/318; 604/35; 604/36; 604/119

(58) Field of Classification Search
USPC .................................. 604/315, 316, 318, 319
See application file for complete search history.

(56) References Cited

U.S. PATENT DOCUMENTS

| | | | |
|---|---|---|---|
| 4,758,238 A | 7/1988 | Sundblom et al. | ............ 604/319 |
| 4,930,997 A | 6/1990 | Bennett | |
| 5,195,961 A | 3/1993 | Takahashi et al. | .............. 604/35 |
| 5,499,969 A | 3/1996 | Beuchat | |
| 6,958,058 B1 | 10/2005 | Hunter, Sr. et al. | |

FOREIGN PATENT DOCUMENTS

WO    WO 93/17729    9/1993

OTHER PUBLICATIONS

International Search Report (PCTISA/210) and Written Opinion (PCT/ISA/237) mailed on Mar. 15, 2010.

*Primary Examiner* — Tatyana Zalukaeva
*Assistant Examiner* — Ilya Treyger
(74) *Attorney, Agent, or Firm* — Jeffrey B. Powers

(57) ABSTRACT

An aspiration flow control device includes a housing having at least one vacuum port, at least one aspiration port, and an ejection port. The at least one vacuum port is adapted to be connected to a vacuum source, and the aspiration port is adapted to be connected to an aspiration line for receiving fluids from a surgical site. The device further includes a rotating structure having at least three vanes, which structure is configured to rotate within the housing. The at least three vanes divide an enclosed volume within the housing into at least three rotating fluid collection chambers. During rotation of the rotating structure, at least one fluid collection chamber is in communication with at least one vacuum port and the aspiration port through which fluid is received, and at least one other fluid collection chamber is simultaneously in communication with the ejection port through which fluid is expelled.

19 Claims, 4 Drawing Sheets

DEVICE FOR COLLECTION OF ASPIRATED FLUIDS

FIELD

The present invention relates to control of aspiration flow in a surgical pump, and more particularly to control of aspiration fluid flow in a cassette utilized in ophthalmic microsurgical systems.

BACKGROUND

This section provides background information related to the present disclosure which is not necessarily prior art.

Surgical procedures often require a continuous flow of fluids to the surgical site, and aspiration of fluids from the surgical site. In ophthalmic microsurgery, fluids may be aspirated from the operative site utilizing surgical cassettes in which a vacuum is applied to provide for collection of aspirated fluids. The volume of the surgical cassettes used in ophthalmic procedures needs to be sufficiently large to hold an amount of fluid typically aspirated during a particular surgery. However, a large cassette volume may require unwanted delay in a build-up of vacuum before effective aspiration can begin. Prior art systems have overcome this problem by providing collection volumes that are much smaller than the total volume to be collected during surgery. These small collection volumes are required to be emptied several times during surgery. The emptying of the small volumes has typically been accomplished using by using a second pump, such as a peristaltic pump. Accordingly, the use of such surgical cassettes is complicated by the need for both a vacuum pump and a peristaltic pump. Therefore, it would be desirable to provide a fluid collection system that can more effectively control collection of aspirated fluid without the need for a second pump.

SUMMARY

This section provides a general summary of the disclosure, and is not a comprehensive disclosure of its full scope or all of its features. The present disclosure relates to ophthalmic surgical systems that include an aspiration flow control device. According to one aspect of the present disclosure, an aspiration flow control device is provided that includes a housing defining an enclosed volume. The housing has at least one vacuum port adapted to be connected to a vacuum source, at least one aspiration port adapted to be connected to an aspiration line for receiving fluids from a surgical site, and an ejection port. The aspiration flow control device includes a structure configured to rotate within the housing. The rotating structure has at least three vanes that divide the enclosed volume within the housing into at least three rotating fluid collection chambers. During rotation of the structure, at least one fluid collection chamber is in communication with at least one vacuum port and the at least one aspiration port through which fluid is received, and at least one other fluid collection chamber is simultaneously in communication with the ejection port through which fluid is expelled. Rotation of the structure permits the continuous receiving and expelling of aspirated fluids by the at least three fluid collection chambers.

According to another aspect of the present disclosure, a method is provided for the continuous receiving and expelling of aspirated fluids by an aspiration flow control device having a rotating structure with at least three vanes. The at least three vanes define three rotating fluid collection chambers that rotate relative to at least one vacuum port, at least one aspiration port, and an ejection port. The method comprises applying a vacuum to the at least one vacuum port of the aspiration flow control device via a vacuum source, and delivering fluids to the aspiration port via an aspiration line for delivering fluids from a surgical site. The method further comprises continuously rotating the rotating structure such that the fluid collection chambers defined by the structure rotate to a first position. The method further comprises rotating the rotating structure such that the fluid collection chambers defined by the structure rotate to a second position, and rotating the rotating structure to a third position. In this manner, the method provides for continuously rotating the structure through the first, second and third positions. Specifically, the structure is rotated to the first position in which a first fluid collection chamber is in communication with a first vacuum port that evacuates the first fluid collection chamber, a second fluid collection chamber is in communication with a second vacuum port and an aspiration port that feeds fluid into the second fluid collection chamber, and a third fluid collection chamber that has been filled with fluid is in communication with an ejection port for emptying fluid from said third fluid collection chamber into a collection reservoir, such as a bag. The structure further rotates to a second position in which the first fluid collection chamber is in communication with the second vacuum port and the aspiration port that feeds fluid into the first fluid collection chamber, a second fluid collection chamber filled with fluid is now in communication with an ejection port for emptying fluid from the second fluid collection chamber, and a third fluid collection chamber is in communication with the first vacuum port that evacuates the third fluid collection chamber. The structure further rotates to a third position in which the first fluid collection chamber filled with fluid is in communication with the ejection port for emptying fluid from the first fluid collection chamber, the second fluid collection chamber is in communication with the first vacuum port that evacuates the second fluid collection chamber, and a third fluid collection chamber is in communication with the second vacuum port and the aspiration port that feeds fluid into the third fluid collection chamber.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

In the various embodiments, an aspiration flow control device is provided for controlling the flow and collection of fluids aspirated from a surgical site. Generally, the aspiration flow control device includes an enclosed volume having at least one vacuum port, at least one aspiration port, and an ejection port. The at least one vacuum port is adapted to be connected to a vacuum source for applying a vacuum to at least a portion of the enclosed volume. The at least one aspiration port is adapted to be connected to an aspiration line for delivering fluids from a surgical site to the aspiration port. The aspiration flow control device includes a rotating structure having at least three vanes, which rotating structure defines at least three rotating fluid collection chambers within the housing. Each rotating fluid collection chamber rotates relative to the at least one vacuum port, the at least one aspiration port, and the evacuation port. The at least three fluid collection chambers are configured to successively rotate through at least a first position, a second position, and a third position. Each fluid collection chamber rotates to a first position in which one of the fluid collection chambers is in communication with the at least one vacuum port for applying a vacuum therein, a second position in which the one of the fluid collection chambers is in communication with the at least one aspiration port through which fluid is delivered into the one of the fluid collection chambers, and a third position in which collected fluid is in communication with the ejection port through which fluid is expelled.

Figure 1:
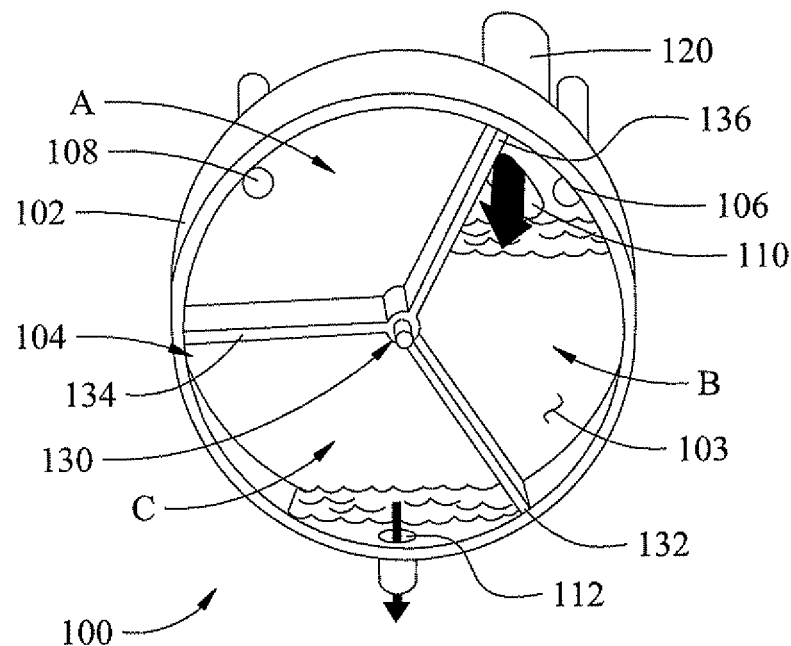
FIG. 1 is a perspective view of a portion of a first embodiment of a fluid collection device for an ophthalmic surgical system in accordance with the principles of the present disclosure.

Referring to FIG. 1, one embodiment of an aspiration flow control device for an ophthalmic surgical system is shown. As shown in FIG. 1, the aspiration flow control device 100 includes a housing 102 defining an enclosed volume 104. The housing 102, shown in FIG. 1 is depicted as a cylindrical housing having a bottom surface 103 and a cover or top (not shown for clarity). The housing 102 may alternatively comprise other shapes or designs that define an enclosed volume therein. The housing 102 further includes a first vacuum port 106 and a second vacuum port 108, at least one aspiration port 110, and an ejection port 112. While the embodiment depicted in FIG. 1 shows at least two vacuum ports 106 and 108, in some applications the housing 102 and/or enclosed volume 104 could alternatively comprise a single vacuum port 106. The vacuum ports 106 and 108 are adapted to be connected to a vacuum source (not shown) for applying a vacuum to at least a portion of the enclosed volume. The aspiration port 110 is adapted to be connected to an aspiration line 120 for receiving fluids from a surgical site (not shown). The ejection port 112 may be a gravity fed ejection port, for example.

Typically, fluids are aspirated from a surgical site through an aspiration line that may be connected to a fluid collection cassette in which a vacuum is created. To hold and contain a large amount of aspirated fluid, a fluid collection cassette must have a sufficient volume. In order for surgery to proceed smoothly, a pump or vacuum source employed to apply a vacuum to the cassette must be able evacuate the cassette volume in a sufficiently short time, which may be called the "vacuum rise time." This "vacuum rise time" for the cassette may be on the order of 1 second for a 500 milliliter volume. Where a vacuum pump or rotary vane pump is used to apply a vacuum to the cassette, the pump needs a working volume that is similar in size to the cassette volume to achieve a short evacuation time. Accordingly, there is a relationship between pump size, vacuum cassette size and vacuum rise time. While it may be desirable to use a very small and low cost vacuum pump in some applications, this would require a small cassette having a correspondingly small volume. Where a vacuum cassette has a volume smaller than the amount of fluid expected to be contained during surgery. The small volume vacuum cassette would need to be continuously emptied by using a second pump as is known in the prior art. Therefore, a vacuum cassette having a small volume requires the complex and costly control of two pumps in concert.

To address the above concern, the first embodiment of an aspiration flow control device 100 further includes a rotating structure 130 configured to rotate within the enclosed volume 104. The rotating structure 130 has at least three vanes 132, 134, and 136 that divide the enclosed volume 104 into regions that act as three separate rotating fluid collection chambers A, B, and C. It is to be understood that edges of vanes 132, 134, and 138 that contact housing 102, bottom surface 103, and the unshown top surface, should form fluid tight seals so that each chamber A, B, and C can be separately evacuated and filled during surgery.

Each fluid collection chamber rotates relative to vacuum ports 106, 108 to at least a first or start position, in which one of the fluid collection chambers is in communication with at least one vacuum port for applying a vacuum to the fluid collection chamber. Each of the fluid collection chambers A, B, and C also rotate relative to aspiration port 110 to at least a second position, in which the one of the fluid collection chambers is in communication with the aspiration port 110 through which fluid is communicated into the fluid collection chamber. Each of the fluid collection chambers A, B, and C also rotate past the vacuum port 106 and aspiration port 110 to a third position, in which the one of the fluid collection chambers is in communication with the ejection port 112 through which fluid is expelled. The vacuum ports 106 and 108, the aspiration port 110, and the ejection port 112 are positioned in the housing 102 relative to the rotating structure 130, such that at least one fluid collection chamber is in communication with both the aspiration port 110 and at least one vacuum port 106 or 108, and at least one other fluid collection chamber is simultaneously in communication with the ejection port 112. As stated before, the three vanes 132, 134, and 136 substantially form a seal relative to the housing, bottom surface 103, and the unshown top surface, so as to provide a seal between each fluid collection chamber relative to the other fluid collection chambers.

In operation, the rotation of the structure 130 (by a motor, not shown) causes the rotating fluid collection chamber A to move to a first position as shown in FIG. 1, where the fluid collection chamber A is evacuated by a vacuum applied via vacuum port 108. Chamber A, at vane 136 is also about to rotate or move over aspiration port 110. Fluid collection chamber B is shown in a position where chamber B is almost full and is about to cease receiving aspirated fluids. Fluid collection chamber C is in a position in which chamber C is in communication with the ejection port 112, through which fluid within chamber C is expelled. The aspiration port 110 shown in FIG. 1 may be large enough to permit delivery of aspirated fluid simultaneously to at least two chambers (A and B, for example) during rotation of the structure 130, to thereby avoid discontinuities in aspiration fluid flow.

Figure 2:
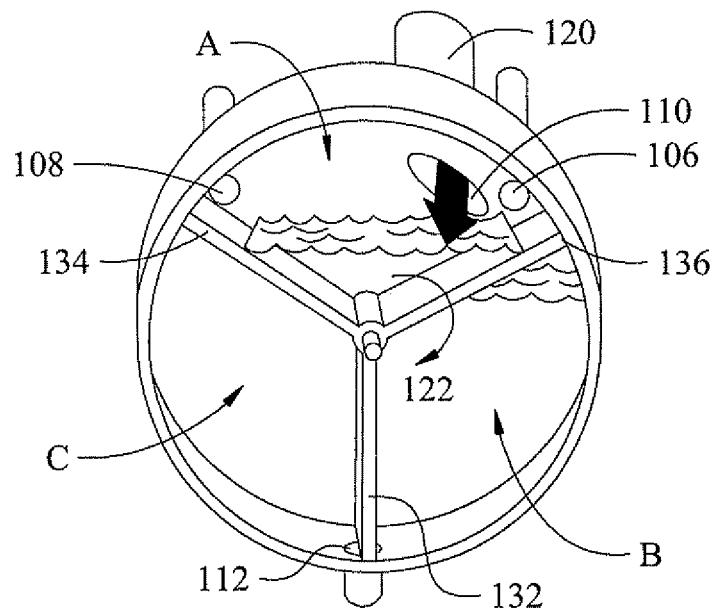
FIG. 2 shows a perspective view of a portion of the fluid collection device in FIG. 1, after clockwise rotation of the vanes.

The rotating structure 130 and vanes 132, 134, and 136 continue to rotate in the direction of the arrow 122, and move to a second position shown in FIG. 2. In this second position, chamber A is still being subjected to an applied vacuum by both vacuum ports 106 and 108. The aspiration port 110 starts to deliver aspirated fluid into chamber A, which is the only chamber receiving aspirated fluid in the second position. As shown in FIG. 2, chamber B is substantially filled with aspirated fluid, and is no longer receiving aspirated fluid since the vane 136 has moved past the aspiration port 110. Chamber B is also about to reach an emptying position as vane 132 is directly over ejection port 112. Chamber C is shown in the ejection position, and substantially all the fluid that may have been within chamber C has exited through ejection port 112. Chamber C is also about to reach the evacuation position once vane 134 rotates past vacuum port 108.

Figure 3:
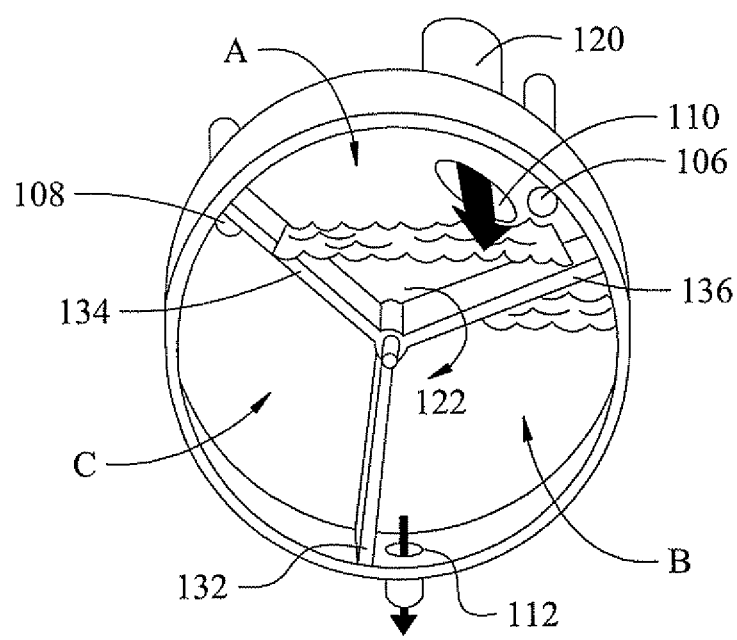
FIG. 3 shows a perspective view of a portion of the fluid collection device in FIG. 1, after further clockwise rotation of the vanes.

The rotating structure 130 and vanes 132, 134, and 136 continue to rotate in the direction of the arrow 122, and move to a third position shown in FIG. 3. Chamber C is now substantially empty, and is being evacuated via vacuum port 108. Chamber B is shown in an emptying position in which aspirated fluids are ejected through the ejection port 112. Chamber A continues to receive aspirated fluids through the aspiration port 110, due to the vacuum created via vacuum port 106. As the rotating structure 130 and vanes 132, 134, and 136 continue to turn, the fluid collection chambers return to the first position depicted in FIG. 1, and the cycle is repeated. Thus, the continuous rotation of structure 130 provides for the continuous receiving and expelling of aspirated fluids by the at least three rotating fluid collection chambers A, B, and C.

Figure 4:
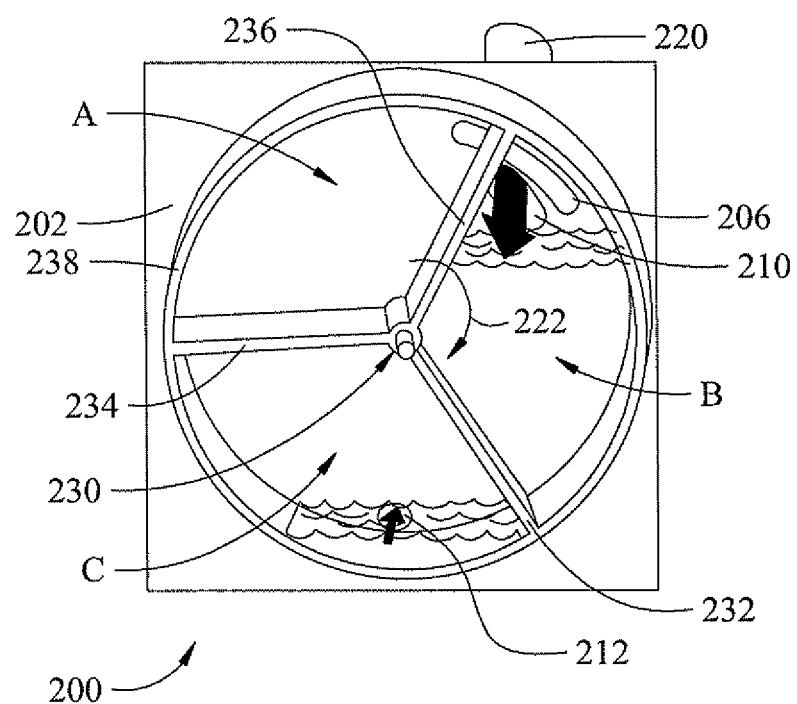
FIG. 4 shows a perspective view of a portion of a second embodiment of a fluid collection device for an ophthalmic surgical system in accordance with the principles of the present disclosure.

Referring to FIG. 4, a second alternate embodiment of an aspiration flow control device 200 is shown. The aspiration flow control device 200 depicted in FIG. 4 shows an interior housing side wall 202 that forms a portion of the overall housing. The housing side wall 202 includes at least one vacuum port 206, at least one an aspiration port 210, and an ejection port 212. The vacuum port 206 is adapted to be connected to a vacuum source (not shown) for applying a vacuum to at least a portion of an enclosed volume within the flow control device 200. The vacuum port 206 shown in FIG. 4 is elongated, to permit the application of a vacuum to one or more chambers, as will be explained below. While the embodiment depicted in FIG. 4 shows a single elongated vacuum port 206, the interior housing wall 202 could alternatively include two separate vacuum ports (such as ports 106 and 108 shown in FIG. 1, for example). The aspiration port 210 is adapted to be connected to an aspiration line 220 for receiving fluids from a surgical site (not shown). The ejection port 212 may be a gravity fed ejection port, for example.

The aspiration flow control device 200 further includes a rotating structure 230 within the housing adjacent the housing side wall 202. The rotating structure 230 has at least three vanes 232, 234, and 236, and an enclosing member 238, which together form three chambers when the rotating structure 230 and housing are covered by a cover or lid (not shown for clarity). The rotating structure 230 is configured to rotate within the housing relative to the interior housing wall 202, the at least one vacuum port 206, the at least one aspiration port 210, and the ejection port 212. The rotating structure 230 has at least three rotating vanes 232, 234, and 236, and the enclosing member 238, and the unshown cover form the three rotating fluid collection chambers A, B, and C. Each of the fluid collection chambers A, B, and C rotate relative to the vacuum port 206, to at least a first position in which one of the fluid collection chambers is in communication with the vacuum port 206 for applying a vacuum to the one fluid collection chamber. Each of the fluid collection chambers A, B, and C also rotate relative to the aspiration port 210, to at least a second position in which the one fluid collection chamber is in communication with the at least one aspiration port through which fluid is communicated. Each of the fluid collection chambers A, B, and C also rotate past the vacuum port 206 and aspiration port 210, to a third position in which the one fluid collection chamber is in communication with the ejection port 212 through which fluid is expelled. The vacuum port 206, aspiration port 210, and ejection port 212 are positioned such that at least one fluid collection chamber is in communication with the vacuum port 206 and the aspiration port 210, and at least one other fluid collection chamber is simultaneously in communication with the ejection port 212 through which fluid within the at least one other fluid collection chamber is expelled. It should be noted that the three vanes 232, 234, and 236, and enclosure member 238, form a vacuum seal with the interior housing wall 202 and unshown cover, to thereby provide three separate fluid collection chambers that are sealed relative to each other.

In operation, the rotating fluid cassette chambers A, B, and C move or rotate past the vacuum port 206, the aspiration port 210, and the ejection port 212 sequentially. The rotation of structure 230 causes the first rotating fluid collection chamber A to move to a first position as shown in FIG. 4, where the fluid collection chamber A may be fully evacuated by a vacuum applied via vacuum port 206. Chamber A is also about to rotate or move over aspiration port 210. Fluid collection chamber B is shown in a position where chamber B is almost full and is about to cease receiving aspirated fluids. Fluid collection chamber C is in a position in which chamber C is in communication with the ejection port 212, through which fluid within chamber C is expelled. The aspiration port 210 may be large enough to permit delivery of aspirated fluid simultaneously to at least two chambers (A and B, for example) during rotation of the structure 230, to thereby to avoid discontinuities in aspiration fluid flow. The vacuum port 206 is elongated to permit application of a vacuum simultaneously to both chamber A and chamber B. This allows for evacuation of chamber A, and for receiving aspirated fluids in chamber B, via the vacuum applied through vacuum port 206.

The rotating structure 230 continues to rotate in the direction of the arrow 222, to a second position similar to that shown in FIG. 2. In this second position, the aspiration port 210 starts to deliver aspirated fluid into chamber A. Chamber B is no longer receiving aspirated fluid since it is not in communication with port 210, Chamber B is also about to reach an emptying position. Chamber C is in an emptying or ejection position, and substantially all of the fluid within Chamber C has exited through ejection port 212.

The rotating structure 230 can rotate further to a third position similar to that shown in FIG. 3. In this third position, where chamber A is receiving aspirated fluid through the aspiration port 210, chamber B is in an emptying position in which aspirated fluids are ejected through the ejection port 212, and chamber C is substantially empty and no longer in communication with ejection port 212. As the rotating structure 230 and vanes 232, 234, and 236 continue to rotate, the fluid collection chambers return to the first position depicted in FIG. 4, and the cycle is repeated. Thus, the continuous rotation of structure 230 provides for the continuous receiving and expelling of aspirated fluids by the at least three rotating fluid collection chambers A, B, and C.

Additionally, either of the above described embodiments may further include a rotating drive mechanism (not shown) coupled to the rotating structure, for effectuating the rotation of the structure defining at least three fluid collection chambers. By controlling the rotating drive mechanism, the structure defining the at least three fluid collection chambers can be rotated at a speed that is sufficient to cause the aspiration flow control device to achieve a vacuum rise time of less than one second. Additionally, the size of the chamber may depend on the maximum flow and the speed of rotation. The faster the vanes rotate, the less time each chamber is exposed to the aspiration port, such that less liquid can be aspirated and the chambers can be smaller. The size of the chamber needs to be balanced with the evacuation step, in which the time that a chamber is in communication with a vacuum port must be greater than the vacuum rise time.

The above devices achieve a small vacuum cassette volume with a continuous or cyclic filling and emptying of aspirated fluid, and therefore, enable the use of a smaller vacuum pump in relation to prior art large volume cassettes. Likewise, the above devices could enable the use of a smaller venturi pump with less consumption of pressurized air. The above designs are beneficial in that they can achieve a high vacuum and fast response time with a very small vacuum pump.

Figure 5:
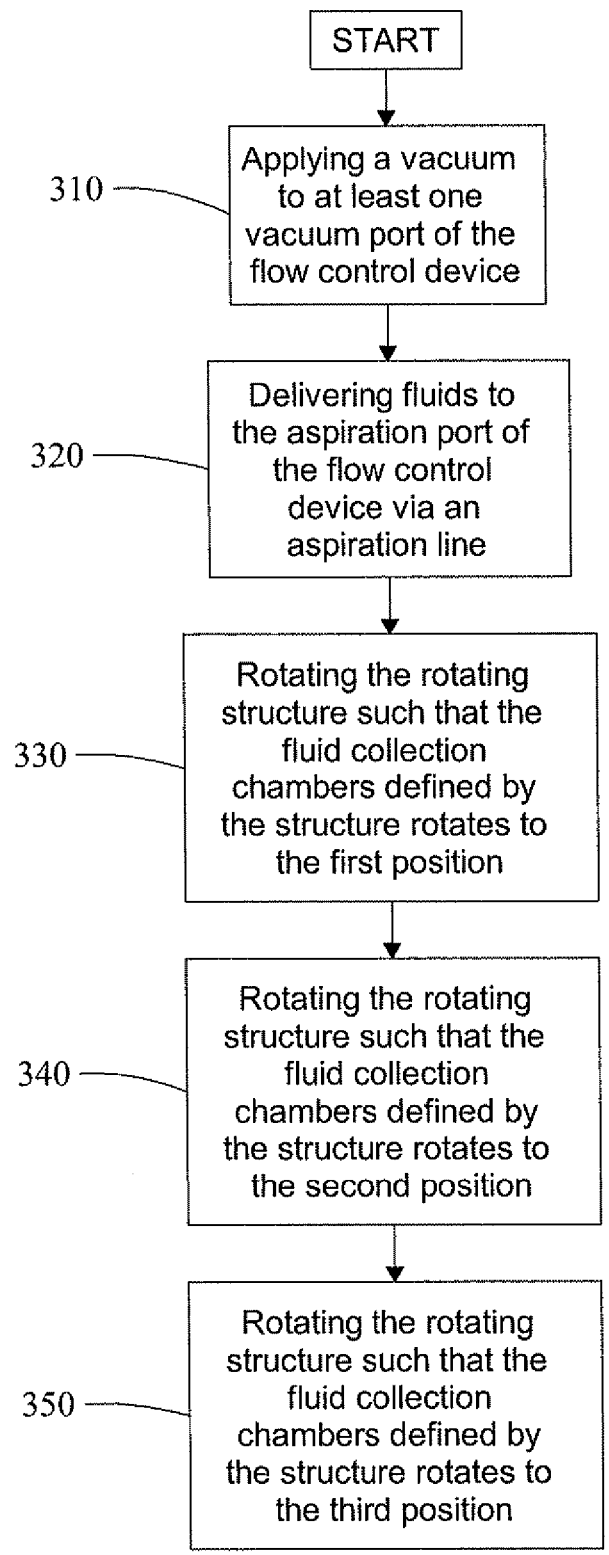
FIG. 5 shows a flow chart describing a method for controlling a fluid collection device to provide the continuous receiving and expelling of aspirated fluids, in accordance with the principles of the present disclosure.

In view of the above embodiments, it may be appreciated that a method for controlling an aspiration flow control device is also provided. The flow chart in FIG. 5 shows one embodiment of a method for providing the continuous receiving and expelling of aspirated fluids by an aspiration flow control device having a rotating structure with at least three vanes defining three rotating fluid collection chambers, which rotates relative to a vacuum port, an aspiration port and an ejection port. The method comprises applying a vacuum to the at least one vacuum port of the aspiration flow control device via a vacuum source, as shown at step 310. The method further comprises delivering fluids to the aspiration port via an aspiration line for delivering fluids from a surgical site at step 320. The method further comprises rotating the rotating structure such that the fluid collection chambers defined by the structure rotate to a first position, at step 330. The method further comprises rotating the rotating structure such that the fluid collection chambers defined by the structure rotate to a second position at step 340, and rotating the rotating structure to a third position at step 350. In this manner, the method provides for continuously rotating the structure through the first, second, and third positions. Specifically, the structure is rotated to the first position in which a first fluid collection chamber is in communication with a vacuum port that evacuates the first fluid collection chamber, a second fluid collection chamber is in communication with the vacuum port and an aspiration port that feeds fluid into the second fluid collection chamber, and a third fluid collection chamber that has been filled with fluid is in communication with an ejection port for emptying fluid from said third fluid collection chamber. The structure further rotates to a second position in which the first fluid collection chamber is in communication with the vacuum port and the aspiration port that feeds fluid into the first fluid collection chamber, the second fluid collection chamber filled with fluid is in communication with the ejection port for emptying fluid from the second fluid collection chamber, and the third fluid collection chamber is in communication with the vacuum port that evacuates the third fluid collection chamber. The structure further rotates to a third position in which the first fluid collection chamber filled with fluid is in communication with the ejection port for emptying fluid from the first fluid collection chamber, the second fluid collection chamber is in communication with the vacuum port that evacuates the second fluid collection chamber, and the third fluid collection chamber is in communication with the vacuum port and the aspiration port that feeds fluid into the third fluid collection chamber.

From the above, it may be appreciated that the present invention provides an improvement to aspiration fluid flow control, to thereby control the flow and collection of fluid aspirated from a surgical site. The present invention is illustrated herein by example, and various modifications may be made by a person of ordinary skill in the art. It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An aspiration flow control device for an ophthalmic microsurgical system comprising:
 a housing defining an enclosed volume, the housing having at least two vacuum ports adapted to be connected to a vacuum source, at least one aspiration port adapted to be connected to an aspiration line for receiving fluids from a surgical site, and an ejection port; and
 a structure configured to rotate within the housing, having at least three vanes that divide the enclosed volume within the housing into at least three rotating fluid collection chambers, wherein during rotation of the structure at least one fluid collection chamber is in communication with the at least one aspiration port and at least one vacuum port, and at least one other fluid collection chamber is simultaneously in communication with the ejection port through which fluid is expelled, whereby rotation of the structure permits continuous receiving and expelling of aspirated fluids by the at least three rotating fluid collection chambers.

2. The aspiration flow control device of claim 1, wherein the structure defining the at least three fluid collection chambers rotates relative to the at least two vacuum ports, the at least one aspiration port through which fluid is communicated into the fluid collection chamber, and the ejection port.

3. The aspiration flow control device of claim 1, wherein the at least two vacuum ports, the at least one aspiration port and ejection port are positioned in the housing relative to the rotating structure such that at least one fluid collection chamber is in communication with both the aspiration port and at least two vacuum, ports, and at least one other fluid collection chamber is simultaneously in communication with the ejection port.

4. The aspiration flow control device of claim 1, wherein the housing is comprised of a cylindrical housing having a bottom and a top that together define an enclosed volume.

5. The aspiration flow control device of claim 4 wherein the three vanes form a seal relative to the cylindrical housing, to thereby provide a seal between each fluid collection chamber relative to the other fluid collection chambers.

6. The aspiration flow control device of claim 1, wherein a vacuum is applied to the at least two vacuum ports.

7. The aspiration flow control device of claim 1, wherein the aspiration port is large enough to enable communication of aspirated fluid into at least two fluid collection chambers simultaneously during rotation of the structure.

8. The aspiration flow control device of claim 1, wherein the ejection port comprises a gravity fed ejection port.

9. The aspiration flow control device of claim 1, wherein the structure is configured to be continuously rotated relative to the at least two vacuum ports, the at least one aspiration port, and the ejection port, to provide for the continuous receiving and expelling of aspirated fluids by the at least three rotating fluid collection chambers.

10. A surgical cassette having an aspiration flow control device, for use in a surgical cassette in an ophthalmic microsurgical system, comprising:

an enclosed volume having at least one vacuum port adapted to be connected to a vacuum source, at least one aspiration port adapted to be connected to an aspiration line for receiving fluids from a surgical site, and an ejection port; and a rotating structure configured to rotate within the enclosed volume relative to the at least one vacuum port, the at least one aspiration port and the ejection port, the rotating structure having at least three rotating vanes that divide the enclosed volume into at least three rotating fluid collection chambers, wherein each fluid collection chamber rotates to at least a first position in which one of the three rotating fluid collection chambers is in communication with the at least one vacuum port for applying a vacuum to the one fluid collection chamber, a second position in which the one fluid collection chamber is in communication with the at least one aspiration port through which fluid is fed into the one fluid collection chamber, and a third position in which the one fluid collection chamber is in communication with the ejection port through which the fluid within the one fluid collection chamber is expelled.

11. The surgical cassette of claim 10, wherein at least one fluid collection chamber is in communication with the at least one aspiration port through which fluid is received and at least one vacuum port, and at least one other fluid collection chamber is simultaneously in communication with the ejection port through which the fluid within the at least one other collection chamber is expelled.

12. The aspiration flow control device of claim 10, wherein the housing is comprised of a cylindrical housing having a bottom and a top that together define an enclosed volume.

13. The aspiration flow control device of claim 12 wherein the three vanes form a seal relative to the cylindrical housing, to thereby provide a seal between each fluid collection chamber relative to the other fluid collection chambers.

14. The aspiration flow control device of claim 10, wherein a vacuum is applied to the at least one vacuum port of the aspiration flow control device.

15. The aspiration flow control device of claim 10, wherein the aspiration port is large enough to enable communication of aspirated fluid into at least two fluid collection chambers simultaneously during rotation of the rotating structure.

16. The aspiration flow control device of claim 10, wherein the ejection port comprises a gravity fed ejection port.

17. The aspiration flow control device of claim 10, wherein each fluid collection chamber rotates sequentially past the at least one vacuum port, the at least one aspiration port, and the ejection port positioned in the enclosed volume.

18. The aspiration flow control device of claim 10, wherein the at least one vacuum port, the at least one aspiration port and the ejection port are positioned in the enclosed volume relative to the rotating structure such that at least one fluid collection chamber is in communication with both the aspiration port and at least one vacuum port, and at least one other fluid collection chamber is simultaneously in communication with the ejection port.

19. The aspiration flow control device of claim 10, wherein the rotating structure is configured to be continuously rotated relative to the at least one vacuum port, the at least one aspiration port, and the ejection port, to provide for the continuous receiving and expelling of aspirated fluids by the at least three rotating fluid collection chambers.

* * * * *